(12) United States Patent
Wallace

(10) Patent No.: US 10,045,838 B2
(45) Date of Patent: Aug. 14, 2018

(54) METHOD OF MAKING A DENTURE

(71) Applicant: Larell Surgical Consultants, Inc., Carmel Valley, CA (US)

(72) Inventor: Lawrence Norman Wallace, Carmel Valley, CA (US)

(73) Assignee: Larell Surgical Consultants, Inc., Carmel Valley, CA (US)

( * ) Notice: Subject to any disclaimer, the term of this patent is extended or adjusted under 35 U.S.C. 154(b) by 0 days.

(21) Appl. No.: 15/790,309

(22) Filed: Oct. 23, 2017

(65) Prior Publication Data

US 2018/0104027 A1 Apr. 19, 2018

Related U.S. Application Data

(63) Continuation of application No. 15/666,172, filed on Aug. 1, 2017, now Pat. No. 9,795,463, which is a continuation of application No. 12/743,780, filed as application No. PCT/US2008/084092 on Nov. 19, 2008, now Pat. No. 9,750,584.

(60) Provisional application No. 61/003,816, filed on Nov. 20, 2007.

(51) Int. Cl.
*A61C 3/08* (2006.01)
*A61C 13/107* (2006.01)

(52) U.S. Cl.
CPC ................. *A61C 13/0001* (2013.01)

(58) Field of Classification Search
CPC ..................... A61C 13/0001–13/003
USPC .............................. 433/168.1–172
See application file for complete search history.

(56) References Cited

U.S. PATENT DOCUMENTS

| 2,685,133 A | 8/1954 | Greene et al. |
| 3,644,996 A | 2/1972 | Weinkle |
| 3,659,344 A | 5/1972 | Gavazzi |
| 3,667,123 A | 6/1972 | Huey |
| 3,838,513 A | 10/1974 | Katz et al. |
| 3,839,796 A | 10/1974 | Hazar |

(Continued)

FOREIGN PATENT DOCUMENTS

WO   WO 2015/120010   8/2015

OTHER PUBLICATIONS

Leinfelder, Karl F., Douglas A. Terry, and Mark E. Connelly. "The Art of Denture Relining." Inside Dentistry 3.5 (2007).

(Continued)

*Primary Examiner* — Yogesh Patel
(74) *Attorney, Agent, or Firm* — Knobbe, Martens, Olson & Bear, LLP

(57) ABSTRACT

A denture is manufactured in a single visit using a preformed dental template chosen from a plurality of different sized dental templates, based on the size of a patient's alveolar edentulous ridge. The dental template includes a base acrylic with prosthetic teeth attached thereto. A viscous material such as an acrylic is added to the selected dental template and the dental template with the added viscous material is placed on the patient's alveolar edentulous ridge. The viscous material is then allowed to solidify to form a rigid or semi-rigid material with the template in proper position in three planes and properly border molded. After solidification a denture is formed that consists of a first base acrylic portion in conterminous relation with a second portion formed of the solidified material that had been added as a viscous material, and with teeth joined to the base acrylic portion.

19 Claims, 5 Drawing Sheets

(56) References Cited

U.S. PATENT DOCUMENTS

| | | | |
|---|---|---|---|
| 3,987,546 A | 10/1976 | Trampe | |
| 4,003,132 A | 1/1977 | Beck | |
| 4,017,971 A | 4/1977 | Hazar | |
| 4,094,067 A | 6/1978 | Hazar | |
| 4,161,065 A * | 7/1979 | Gigante | A61C 13/1013 264/18 |
| 4,175,322 A * | 11/1979 | Tureaud | A61C 13/00 433/171 |
| 4,245,988 A | 1/1981 | Cinotti et al. | |
| 4,247,287 A | 1/1981 | Gigante | |
| 4,457,713 A | 7/1984 | Schneider | |
| 4,583,947 A | 4/1986 | Hazar | |
| 4,657,509 A | 4/1987 | Morris | |
| 4,661,065 A | 4/1987 | Gettleman et al. | |
| 4,681,543 A * | 7/1987 | Monroy | A61C 13/00 264/18 |
| 5,304,062 A | 4/1994 | Saitoh et al. | |
| 5,431,563 A | 7/1995 | Huybrechts | |
| 5,513,988 A | 5/1996 | Jeffer et al. | |
| 5,775,900 A | 7/1998 | Ginsburg et al. | |
| 5,885,077 A | 3/1999 | Jeffer | |
| 6,079,981 A | 6/2000 | Sekendur | |
| 6,655,962 B1 * | 12/2003 | Kennard | A61C 8/0022 433/174 |
| 9,750,584 B2 | 9/2017 | Wallace | |
| 9,795,463 B1 | 10/2017 | Wallace | |
| 2003/0162147 A1 | 8/2003 | Dequeker | |
| 2007/0071736 A1 | 3/2007 | Elia | |
| 2007/0183572 A1 | 8/2007 | Drummond et al. | |
| 2010/0297581 A1 | 11/2010 | Wallace | |
| 2012/0258430 A1 | 10/2012 | Ruppert et al. | |
| 2012/0276502 A1 | 11/2012 | Marshall | |
| 2015/0147719 A1 | 5/2015 | Wallace | |
| 2015/0327962 A1 | 11/2015 | Ginsburg et al. | |

OTHER PUBLICATIONS

PermaSoft Soft Denture Liner Directions for Use, Laboratory Technique, Chairside Technique, *Dentsply Austenal* dated 2004 in 11 pages.

The Three Appointment Denture Technique as Presented by Robert H. Griffiths, D.D.S. and Don Kaylor, CD. T., printed by the Council on Prosthetic Services and Dental Laboratory Relations in May 1979, in a pamphlet entitled Compilation of Reduced Fee Denture Techniques in 2 pages.

International Search Report and Written Opinion dated Jan. 12, 2009 in 5 pages in PCT Application No. PCT/US08/84092.

International Search Report and Written Opinion dated Feb. 26, 2015 in 6 pages in PCT Application No. PCT/US2014/067770.

* cited by examiner

METHOD OF MAKING A DENTURE

BACKGROUND OF THE INVENTION

Field of the Invention

The present invention relates to medical devices and, more specifically to dentures and a method for fabricating a denture in one visit.

Description of the Related Art

Many patients require dentures but do not have easy access to dental care, either because of monetary limitations or geographical limitations. Many patients are older and live in nursing homes or assisted living facilities, making it difficult for those patients to go to the dentist's office once, let alone visit the office four to five times as required for conventional dentures. Additionally, conventional dentures are expensive and not fully covered by insurance and not covered at all by Medicare. Nonetheless, functional dentures are important in maintaining general health, decreasing the incidence of chronic disease, lowering overall medical costs while offering a higher quality of life and sense of self-esteem.

Missing teeth have a variety of implications, including impairment of mastication, speech defects, swallowing disorders, nutrition intake, distorted facial contour, and overall physical and emotional discomfort. Headaches and other illnesses are often related to missing teeth. Replacement of missing teeth is therefore a necessity that is significant to emotional and physical health and well being.

Conventional dentures are fabricated in dental offices and typically require four to five visits by the patient. During the first visit at the dentist's office, a preliminary impression is taken to make a custom mold of the mouth. That mold may be sent to the laboratory to make custom impression trays. During the second visit to the dentist, the custom impression trays are checked and adjusted and the dentist also takes final impressions. The corresponding laboratory procedures involve creating a cast master mold, a stabilized based plate, and a wax occlusal rim. During the third visit to the dentist, the dentist determines the maxilio-mandibular relation, selects the teeth for the denture, and takes a bite registration. The corresponding laboratory work involves setting the anterior and posterior teeth, thus completing a wax denture for the patient to try. During the fourth visit to the dentist, the dentist checks the aesthetics and functionality of the wax up dentures, checks the occlusal and vertical dimension, and makes any required corrections. The dentures are sent to the lab to be processed and finished. The fifth visit to the dentist involves the delivery of the dentures, a final check for fit and then, finally, the dentures are given to the patient for home use.

One article suggests that the process of fabricating a denture can be accomplished in three appointments. This procedure is described in the article entitled *The Three Appointment Denture Technique* as Presented by Robert H. Griffiths, D.D.S. and Don Kaylor, C.D.T., printed by the Council on Prosthetic Services and Dental Laboratory Relations in May 1979, in a pamphlet entitled *Compilation of Reduced Fee Denture Techniques*. In the first, 45 minute appointment, the dentist conducts an examination of the patient which involves examining the tissue and structures, taking a panoramic radiograph, discussing patient history, selecting impression trays, taking facial measurements, determining the tentative vertical and centric relationship, and selecting the teeth and teeth shades. Stabilized base plates should then be received from the lab so that a wax-up can occur. During the second, 20 minute appointment, a preliminary fit analysis of the wax setup occurs and necessary adjustments are made. Between the second and third appointments, the lab must complete the final set of dentures. The third, 20 minute appointment, involves checking the final set of dentures and instructing the patient on how to use the dentures.

Most notably, the proposed three visit procedure only results in a cost saving when the dentist office is able to work closely with the dental laboratory. Additionally, the procedure still requires making a wax model for the first try-in. Making a wax setup requires a significant amount of time and expense.

Sekendur, U.S. Pat. No. 6,079,981, discloses a method for making a customized denture from standard sized segments of prefabricated prosthetic teeth which may be joined and adjusted to fit an individual's mouth. Each prosthetic tooth is bonded to a prosthetic gum segment. The gum segments of each prosthetic tooth are joined to form the gum line. The prosthetic teeth are first selected and then evaluated in the patient's mouth by the dentist, conformed in the mouth or on a model of the mouth to form the denture, and finally cured to form the finished denture.

Saitoh, et. al., U.S. Pat. No. 5,304,062, discloses a prosthetic denture precursor and a method for making the same. The prosthetic denture precursor comprises at least one artificial tooth and a photopolymerizable denture base material which holds the root portion of the artificial tooth. The method of making the prosthetic denture precursor does not require making a wax denture, as the photopolymerizable denture base can be deformed prior to exposure to light. After the tooth is adjusted to a dentally operative position, the base is irreversibly hardened by exposure to light.

Hazar, et al., U.S. Pat. No. 4,583,947, discloses a custom denture and method for making the same. A standard-sized base is selected and fitted with artificial teeth. The teeth are fit into the base and secured by a Li-shaped appliance which stabilizes the teeth in their relative positions in the sockets. To determine the appropriate standard base size to select, the dentist takes an impression of the patient's oral cavity. From the impression, upper and lower models are cast, allowing the dentist to select the most appropriate standard-sized base. The bases are then conformed to the surface contours using the casted models and finally, the artificial teeth are secured.

Other methods of making custom dentures have failed to fully address the issue of being able to produce the dental device in a single visit and doing so at a reduced cost, such as may be at the level of Medicaid reimbursement. Thus, patients who do not have easy access to a dental office and those who cannot afford the procedure are precluded from dental treatment which is necessary for physical and emotional health. Furthermore, many dentists choose not to make dentures because the process requiring multiple visits is not profitable. Other methods also require the use of an off-site dental laboratory, adding to time and cost.

It would therefore be desirable to provide a custom denture that overcomes the shortcomings and limitations of conventional dentures and the conventional methods for making dentures

BRIEF SUMMARY OF THE INVENTION

To address these and other needs, and in view of its purposes, one aspect of the present invention provides a pre-formed denture template with teeth in place, and which requires only one step and only one sitting, to be made into a finalized, customized denture. The sitting may be a visit to a dental office according to one exemplary embodiment.

According to one aspect, the invention provides a method for forming a denture for a patient in a single dental office visit. The method comprises providing a plurality of denture templates having different sizes, each having been pre-formed to a pre-formed shape and comprising a base acrylic portion with prosthetic teeth adjoined thereto, selecting a first dental template of the plurality of dental templates that has a size generally corresponding to a size of the patient's edentulous alveolar ridge but does not fit conformably, i.e., exactly thereto. The method further comprises adding an impression material which may be a reline or other viscous material, to the first dental template and positioning the first dental template on the patient's edentulous alveolar ridge to mold the impression material to conform to the contours of the patient's edentulous alveolar ridge and vestibule. The method further comprises allowing the impression material to solidify to produce a customized, rigid or semi-rigid molded portion thereby forming a denture comprised of the prosthetic teeth, the base acrylic portion and the solidified molded portion which includes a custom lining. The steps of selecting, adding, positioning and allowing may advantageously take place in one visit.

According to another aspect, the present invention provides a denture formed according to such method and including two acrylic sections. A template is formed of a first acrylic portion and includes teeth coupled directly to the first acrylic portion. A second acrylic portion is conterminous with the first acrylic portion and conforms to a patient's edentulous alveolar ridge and may be rigid or semi-rigid.

According to another aspect, the invention provides a denture comprising teeth and a denture base consisting of two acrylic portions including a template fainted of a first acrylic portion and coupled directly to the teeth and a second acrylic portion adjacent and conterminous with the first acrylic portion and being conformed to a patient's edentulous alveolar ridge.

BRIEF DESCRIPTION OF THE SEVERAL VIEWS OF THE DRAWINGS

The present invention is best understood from the following detailed description when read in conjunction with the accompanying drawings. It is emphasized that, according to common practice, the various features of the drawings are not necessarily to scale. On the contrary, the dimensions of the various features may be arbitrarily expanded or reduced for clarity. Like numerals denote like features throughout the specification and drawings.

FIG. 2A is a perspective view of the exemplary maxillary denture template, FIG. 2B is a side view of the exemplary maxillary denture template. FIG. 2C is a front view of the exemplary maxillary denture template. FIG. 2D is a cross-sectional view of the exemplary maxillary denture template.

FIG. 5A is a perspective view of the exemplary maxillary denture formed in accordance with the present invention. FIG. 5B is a side view of the exemplary maxillary denture formed in accordance with the present invention. FIG. 5C is a front view of the exemplary maxillary denture and FIG. 5D is a cross-sectional view of the exemplary maxillary denture formed in accordance with the present invention.

DETAILED DESCRIPTION OF THE INVENTION

The present invention provides for making a dente a patient from a pre-formed denture template device, in one sitting such as a visit to a dental office or another location.

Figure 1:
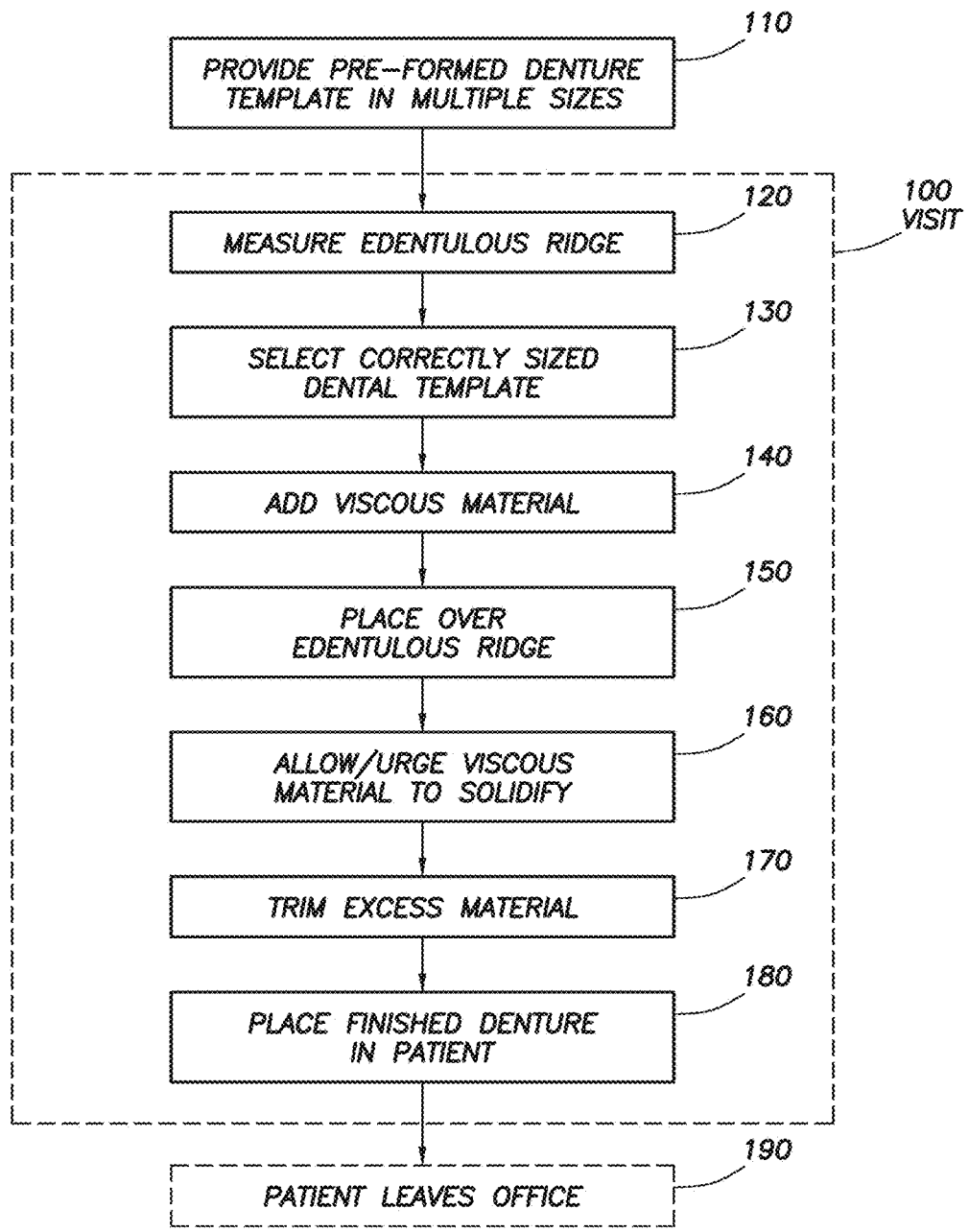
FIG. 1 is a flowchart illustrating the process for producing a denture in one office visit in accordance with the invention.

Referring to FIG. 1, prior to the patient's office visit 100, pre-formed dental templates are provided in multiple standard sizes at step 110. At step 120, the patient's edentulous alveolar ridge is measured and at step 130, the appropriately sized dental template is selected. Viscous material such as an acrylic is added at step 140 and the denture template with the viscous material is placed over the edentulous alveolar ridge of the patient at step 150 and serves as an impression material. At step 160, the viscous material is allowed to solidify to form the denture. At step 170, the excess solidified material is trimmed and at step 180, the finished denture is worn by the patient. The manufacture of the denture is complete in one office visit. At step 190, the patient leaves the dental office with the customized, finished denture as formed in one office visit. Note that the above flowchart illustrates one exemplary method for forming the completed denture but various variations and further details of the process are also within the purview of the invention and are disclosed herein, in conjunction with the following figures.

Figure 3:
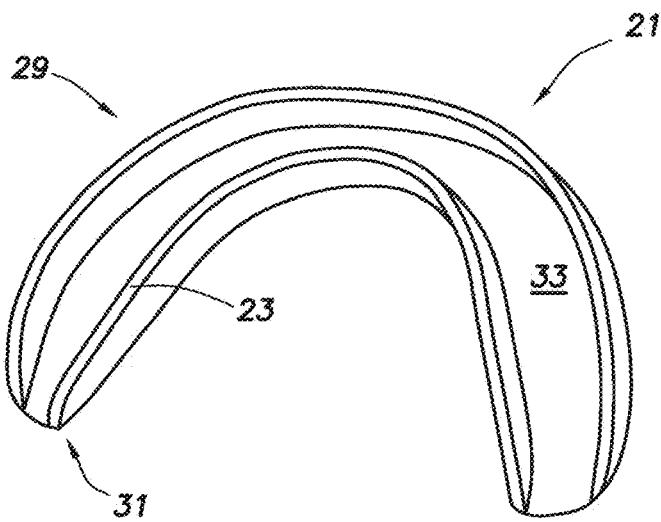
FIG. 3 is a perspective view of an exemplary mandibular denture template in accordance with the present invention.
Figure 4:
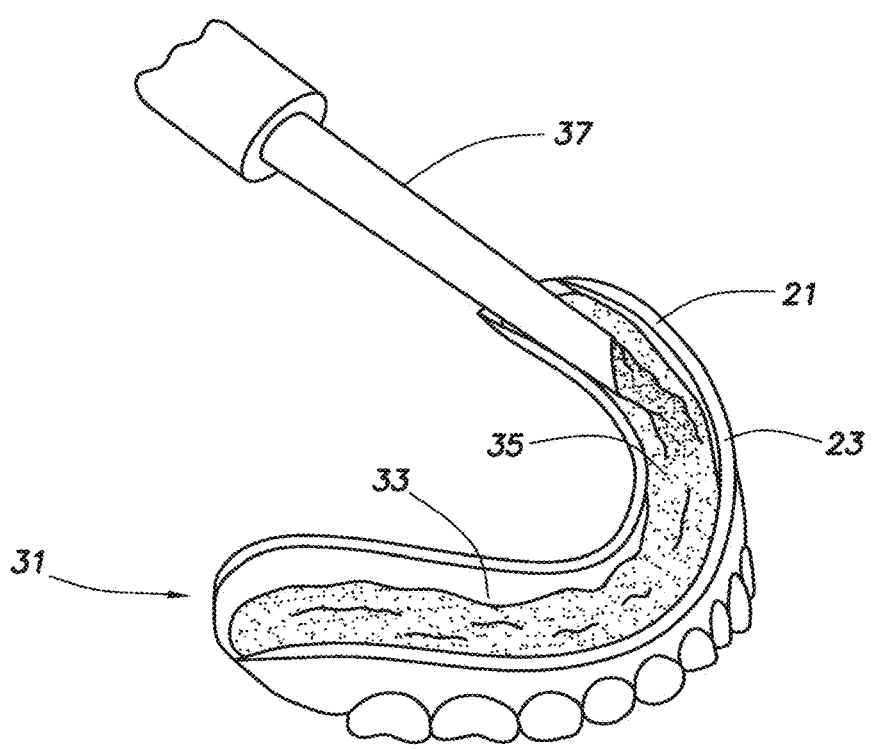
FIG. 4 is a perspective view illustrating a viscous material added to the mandibular denture template shown in FIG. 3.

FIGS. 2A-2D illustrate an exemplary pre-formed dental template in accordance with the invention. FIGS. 2A-2D illustrate a maxillary denture template used to produce the maxillary denture shown in FIGS. 5A-5D but it should be understood that the method of the invention can be can be practiced upon a mandibular denture template such as shown in FIGS. 3 and 4, to produce a final customized mandibular denture. The inventive method of manufacturing a denture from a dental template is substantially similar for the mandibular and the maxillary units, with some distinctions noted in the following detailed description.

Figure 2A:
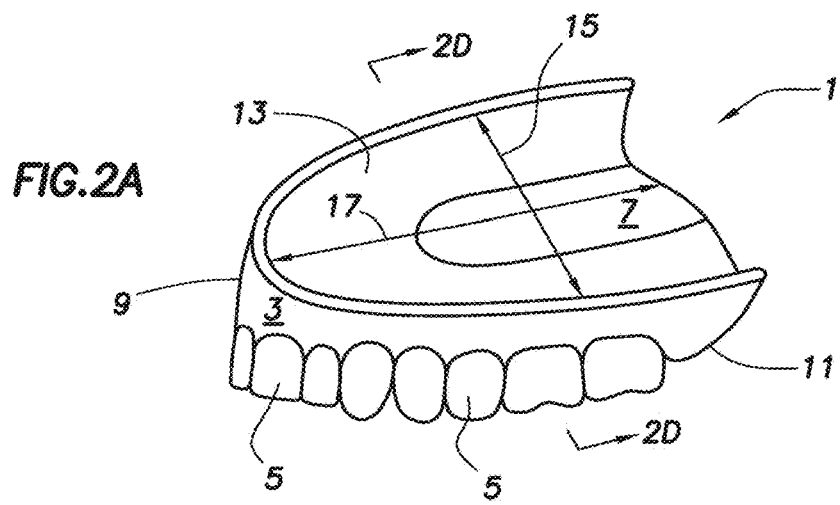
FIGS. 2A-2D illustrate an exemplary maxillary denture template in accordance with the present invention.
Figure 2B:
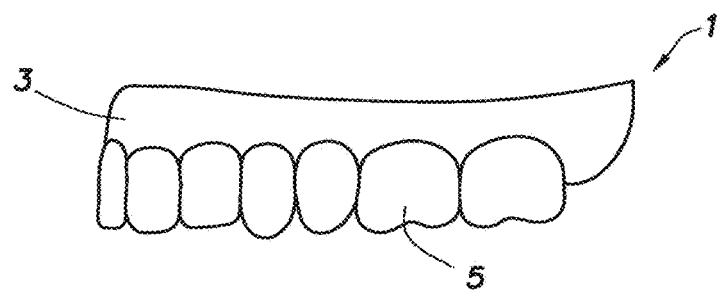
Figure 2C:
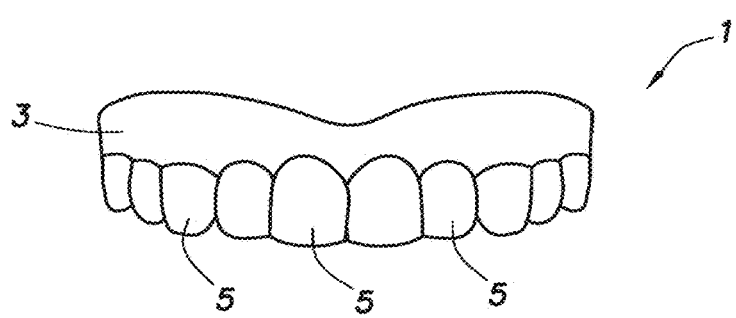
Figure 2D:
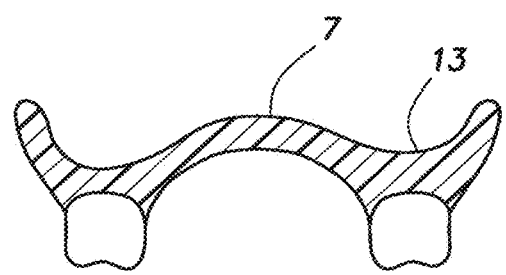

FIGS. 2A-2D illustrate exemplary maxillary denture template 1 from which a denture will be made. Maxillary denture template 1 is not sized or contoured to be in suitable condition to be worn as a denture but, rather, is pre-formed to a standard size. FIG. 2D is a cross-sectional view taken along line 2D-2D of FIG. 2A. Maxillary denture template 1 is formed of an acrylic referred to as base acrylic 3 to distinguish it from another acrylic portion that may preferably be added. Teeth 5 are already joined to base acrylic 3 in pre-formed maxillary dental template 1. Teeth 5 are conventional prosthetic teeth preferably all of the same color, typically shade 65, although any of various other shades may be used in other exemplary embodiments. Teeth 5 may be formed of various suitable conventional materials used in the dental arts. Base acrylic 3 may be formed of various suitable dental acrylics available in the dental arts. In one exemplary embodiment, the acrylic may be a long-chain methyl methacrylate polymer. Methyl methacrylate is an inorganic compound with the formula $CH_2\!=\!C(CH_3)$ $CO_2CH_3$. In other exemplary embodiments, other suitable dental acrylics such as thermoplastic resins and semi-rigid reline materials may be used as base acrylic 3.

Maxillary dental template 1 includes palatal vault 7 and is defined by anterior 9 and posterior 11. The palatal vault is not present in the mandibular dental template embodiment, as will be seen in FIGS. 3 and 4. Channel 13 is a valley that is generally u-shaped and extends about maxillary denture template 1 corresponding to and for receiving the patient's edentulous alveolar ridge. Channel 13 generally takes the shape of a trough and may have a generally u-shaped cross-section or other similar and suitable cross-sections for receiving the patient's edentulous alveolar ridge. As will be shown, channel 13 of maxillary denture template 1 is only generally shaped and sized to receive the patient's edentulous alveolar ridge and only when additional acrylic or other viscous material is added to complete the denture as will be shown, will channel 13 have a suitably conformal size and shape defined by the added material, and be ready to be worn as a denture. Maxillary dental template 1 is pre-formed to a plurality of standard sizes that may be held in inventory by the dental practitioner.

When a patient with one or two edentulous alveolar ridges enters the dentist's office or onsite location for a single dental visit, the dentist will have stocked a plurality of different-sized pre-formed maxillary and mandibular dental templates. According to one exemplary embodiment, there may be four different sizes of each of the pre-formed dental templates and in another exemplary embodiment, there may be at least three different sizes, i.e., small, medium and large pre-formed dental templates, possessed by the dentist, but various numbers of differently-sized dental templates may be available in exemplary embodiments. The patient is first examined. Once it is determined no gross pathology exists, a suitably sized pre-formed denture template such as maxillary denture template 1 is chosen according to the embodiment in which the patient's edentulous ridge is the upper alveolar ridge. The proper maxillary denture template 1 size is based on sizes such as width 15 and length 17 and is chosen to minimize the amount of free space between denture template 1 and the edentulous ridge. The width of the patient's maxillary ridge and other measurements may be recorded and taken into account in selecting the appropriately sized maxillary denture template 1. The size of maxillary denture template 1 is chosen to preferably allow the upper posterior teeth to be positioned over the center of the patient's maxillary ridge. The selected maxillary denture template 1 may have a size most closely resembling the size of the patient's anatomy. After the appropriately sized pre-formed denture template 1 is selected from the plurality of dental template sizes available, maxillary denture template 1 is then formed into a final maxillary denture customized to the patient by next adding an impression material such as a further acrylic, which will be in viscous form when added to maxillary dental template 1. According to one embodiment, a device similar to a Fox plate may be placed in the mouth against the teeth of the denture device in the patient's mouth. With such a device in place, the ala-tragal line can be followed for the correct occlusal plane angle in a superior inferior dimension. The occlusal plane in a coronal dimension may also be noted with this device, to ensure that the occlusal plane matches the pupillary plane of the patient's eyes. Various other measurement and adjustment techniques may be used in various exemplary embodiments.

The addition of viscous impression material will now be shown with respect to a mandibular dental template in FIGS. 3 and 4.

FIG. 3 shows mandibular dental template 21, to which a further material will be added in viscous form. Mandibular dental template 21 is formed of base acrylic 23 and is defined by anterior 29 and posterior 31. Base acrylic 23 may be formed of the materials described in conjunction with base acrylic 3. Channel 33 generally receives the patient's mandibular edentulous ridge. To manufacture a custom-fit denture from pre-formed mandibular dental template 21, a further acrylic or other material is chosen to be added to mandibular denture template 21, in particular within channel 33 to serve as an impression material. The further material that will be added to base acrylic 23 to form the denture, is an impression material that is viscous when added to mandibular denture template 21 and will later be allowed to solidify by cooling, air drying, curing or by use of other suitable means, depending on the type of further material used.

FIG. 4 shows viscous material 35 being added to mandibular denture template 21. In particular, viscous material 35 is added into channel 33. Various suitable acrylic or other materials may be used as viscous material 35. In one exemplary embodiment, methyl methacrylate may be used. Other suitable acrylics such as thermoplastic acrylics may be used. In still other exemplary embodiments, conventional dental materials such as thermoplastic resins and various suitable reline materials may be used. Various other plastics and other biologically compatible materials may also be used in other exemplary embodiments. Many other appropriate materials are also available as conventional reline material in the dental prosthetics field and may be used.

Appropriate amounts of viscous material 35 are added to mandibular denture template 21 and various degrees of viscosity may be used. Viscous material 35 may be a gel, paste or other suitable composition and serves as an impression material. One commonly used material is a powder/liquid combination which may be a monomer and polymer combination that sets to a firm but resilient consistency. Alternatively stated, the initially viscous material 35 may solidify to form a semi-rigid material according to one exemplary embodiment. According to another exemplary embodiment, the initially viscous material 35 may solidify to form a rigid material. The extent of the firmness can be based on the ratio of the powder/liquid mix. For edentulous ridges that are smaller or include more friable tissue, the mix may be chosen for a softer consistency. For larger edentulous ridges with healthy tissue, the mix may be chosen to produce a firmer consistency. The type of material chosen for the patient may depend on the examination and amount of available edentulous ridge.

Two exemplary acrylic reline materials that form semi-rigid materials upon solidification, i.e., they retain some elasticity and compressibility, include MucoSOFT by Parkell Corporation of Edgewood, N.Y. and PermaSoft by Dentsply Corporation of York, Pa. Materials that form rigid materials upon solidification include MucoHARD by Parka Corporation and Triad by Dentsply Corporation. Other suitable and commercially available materials may be used in other exemplary embodiments.

Various suitable conventional means may be used to introduce viscous material 35 into mandibular denture template 21. In one exemplary embodiment, dispenser 37 may be used to direct viscous material 35 into channel 33 of mandibular denture template 21. According to various exemplary embodiments, the components that combine to form viscous material 35 may be mixed such as in a mixing tube within dispenser 37. Other techniques for forming and directing viscous material 35 to mandibular denture template 21 may be used in other exemplary embodiments. Appropriate amounts of viscous material 35 are applied to mandibular denture template 21, being certain that there is a sufficient amount at the flanges to fully allow accurate border molding, a sufficient amount at posterior 31 to form a post dam if needed and a sufficient amount to prevent air bubbles.

Mandibular denture template 21 with viscous material 35 is then seated on the appropriate alveolar edentulous ridge in the mouth. Conventional techniques for applying suitable pressure may be used. Anterior and posterior positioning relative to the patient's upper lip may be initially carried out then checked. After the anterior/posterior positioning is carried out, further positioning is carried out.

During this time, the mandibular denture template 21 with viscous material 35 is seated on the edentulous ridge of the patient and the impression material, viscous material 35, conforms to the anatomy of the patient's edentulous ridge. Mandibular denture template 21 is fitted in the mouth to assure that there is minimal space between mandibular denture template 21 and the edentulous ridge of the patient and with sufficient pressure to produce a customized conformal denture and to force out any excess viscous material 35. After all the adjustments are carried out and the position of the mandibular denture template 21 has been determined to be correct in all three dimensions, functional border molding may be done. Conventional border molding techniques may be used. According to one exemplary embodiment, the border molding may be first done in the posterior flange areas, next in the canine areas and then in the anterior portion. Once viscous material 35 takes on the shape of the patient's anatomy after it has been finally positioned correctly and begins to solidify, the apparatus, i.e., mandibular denture template 21 with viscous material 35, is removed from the patient's mouth and excess viscous material 35 can be optimally trimmed from the buccal flange areas at this stage. The conformal, inner surface of viscous material 35 is checked for voids and to determine if any areas are void of the added viscous material 35. If any such voids are noted, additional viscous material may be added and the device reinserted and repositioned in the patient's mouth.

The viscous material 35 is then urged to solidify completely and irreversibly. The solidification may be effectuated by the cross-linking of an acrylic material that may advantageously be used, to form a long chain acrylic and this may take place by simply air drying, by cooling, or using other suitable curing techniques such as the light-stimulated curing of a photopolymerizable material to irreversibly harden viscous material 35 to form a solidified material. For other materials, other solidification techniques may be used. Depending on the particular initially viscous material 35 that was used, the solidified material may be a rigid material or a semi-rigid material with some degree of elasticity and compressibility. After solidification is complete and any additional trimming has been carried out, the fabrication of the denture in one visit is complete after checking occlusion, speech, swallowing patterns and flange finish, and the patient leaves with a customized denture.

The previously described sequence and methods apply to either the mandibular or maxillary denture template. According to one exemplary embodiment in which a patient requires both a mandibular and maxillary denture, one advantageous sequence of operations includes first fabricating the maxillary denture and then fabricating the mandibular denture. In this embodiment, the adjustment of the mandibular denture template can be made with proper occlusion to the previously fabricated maxillary denture template.

Figure 5A:
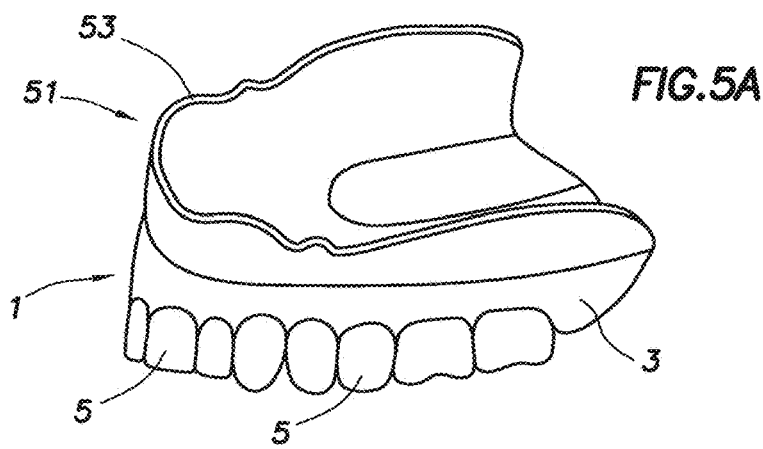
FIGS. 5A to 5D correspond to FIGS. 2A-2D and illustrate an exemplary maxillary denture formed from the exemplary maxillary denture template of FIGS. 2A-2D in accordance with the present invention.
Figure 5B:
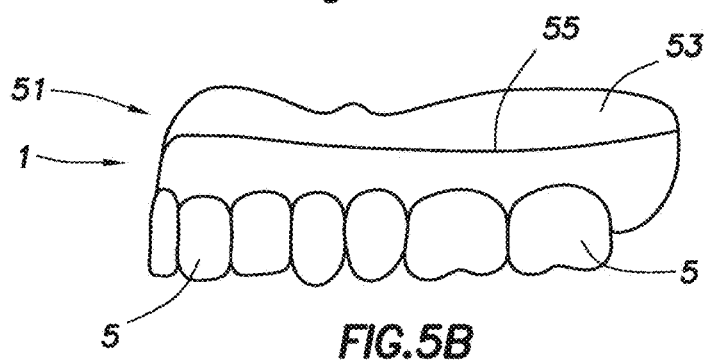
Figure 5C:
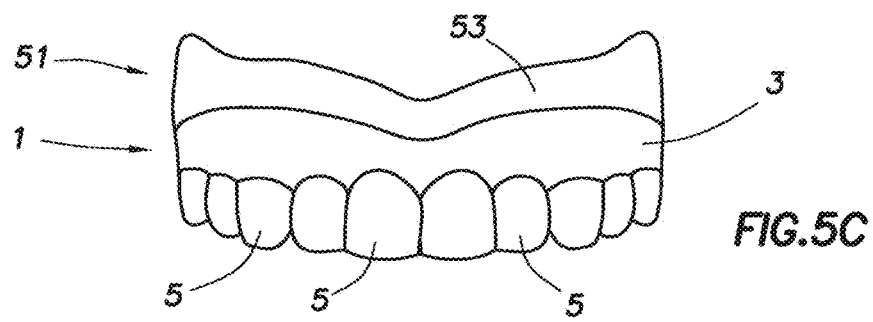
Figure 5D:
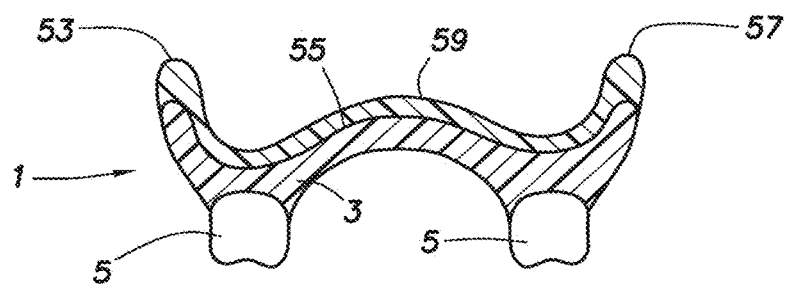

FIGS. 5A-5D show the completed custom maxillary denture formed from the corresponding denture template 1 shown in FIGS. 2A-2D and according to the method described with respect to another embodiment illustrated in FIGS. 3 and 4 which show viscous material 35 added to an exemplary mandibular dental template. Returning to FIGS. 5A-5D, maxillary denture 51 includes a first acrylic portion formed of base acrylic 3 of maxillary denture template 1 and second portion 53 formed of a further material that may preferably be acrylic and which had been added to denture template 1 as a viscous material but was urged or allowed to solidify to form solidified second portion 53 which may be rigid or semi-rigid. In a preferred embodiment, second portion 53 is formed of solidified acrylic. Maxillary denture 51 includes teeth 5. FIG. 5D best illustrates that solidified second material 53 includes buccal flange sections 57 and inner surfaces 59. It should be understood that solidified second material 53 may be formed of a non-acrylic or acrylic material. Base acrylic 3 and solidified second material 53 are in a conterminous relationship, directly contacting at interface 55.

Figure 6:
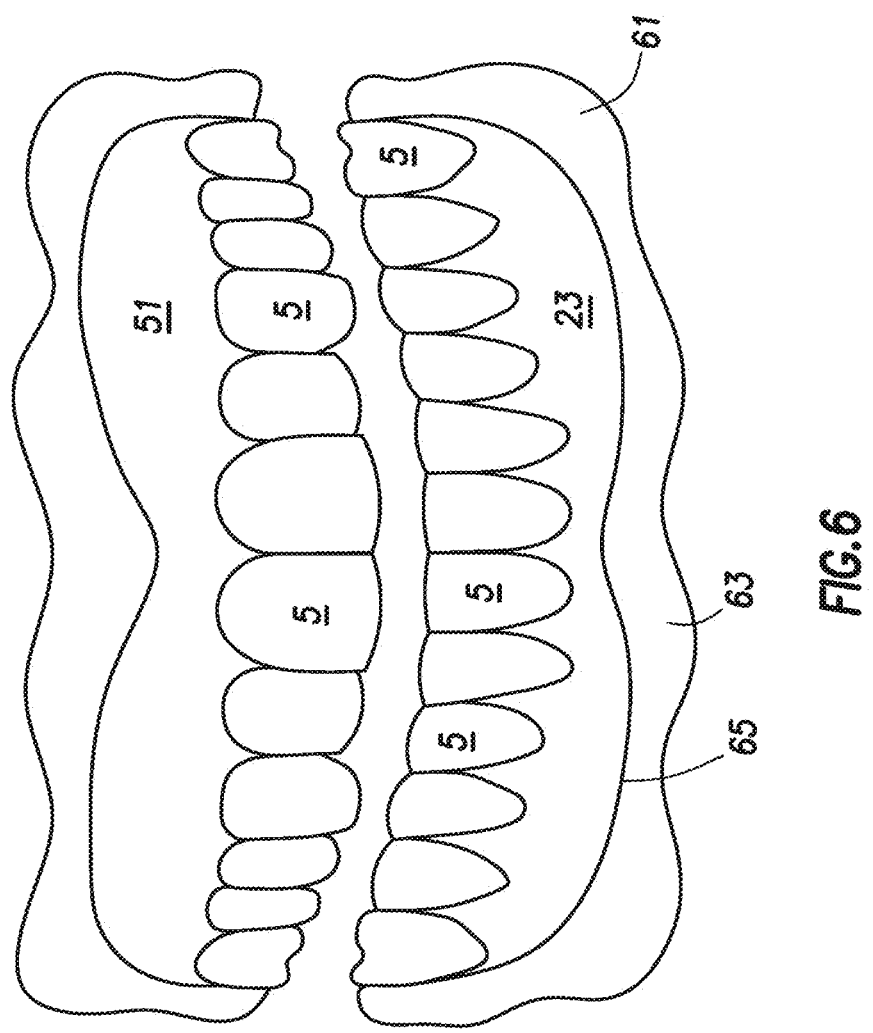
FIG. 6 illustrates a set of exemplary maxillary-mandibular dentures being worn by a patient.

FIG. 6 is a perspective view showing a patient that has been fitted with both a maxillary denture 51 and a mandibular denture 61. As seen most clearly in mandibular denture 61, the denture consists of teeth 5, base acrylic 23 and solidified material 63 such as formed from viscous material 35 shown in FIG. 4 and which may advantageously be an acrylic. Base acrylic 23 and solidified material 63 are conterminous materials and share interface 65.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform in the same function, regardless of structure.

This description of the exemplary embodiments is intended to be read in connection with the figures of the accompanying drawings, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawings under discussion. These relative terms are for convenience of description.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method of producing a denture, said method comprising:
   selecting for a patient having at least one edentulous alveolar ridge a pre-formed denture template from a plurality of pre-formed denture templates, wherein the plurality of pre-formed denture templates comprises pre-formed denture templates of at least two different sizes, wherein each pre-formed denture template of the plurality of pre-formed denture templates comprises:
     a base portion comprising a u-shaped trough generally in the shape of an alveolar ridge and being configured to accept the one edentulous alveolar ridge of the at least one edentulous alveolar ridge into the u-shaped trough, wherein the base portion is formed out of a first material; and
     prosthetic teeth attached to the base portion;
   wherein the pre-formed denture template is selected from the pre-formed denture templates of at least two different sizes to generally correspond to a size of the one edentulous alveolar ridge of the at least one edentulous alveolar ridge;
   placing a viscous second material inside the u-shaped trough, wherein the viscous second material placed inside the u-shaped trough is the same material as the first material out of which the base portion is formed;
   positioning the u-shaped trough containing the viscous second material over the one edentulous alveolar ridge of the at least one edentulous alveolar ridge;
   seating the pre-formed denture template on the one edentulous alveolar ridge of the at least one edentulous alveolar ridge such that the one edentulous alveolar ridge of the at least one edentulous alveolar ridge is pressed into the viscous second material contained within the u-shaped trough thereby conforming a portion of the viscous second material contained within the u-shaped trough to the one edentulous alveolar ridge of the at least one edentulous alveolar ridge; and
   allowing the viscous second material to irreversibly solidify; measuring at least one dimension of the one edentulous alveolar ridge of the at least one edentulous alveolar ridge to obtain at least one measurement of the at least one dimension, wherein the step of selecting the pre-formed denture template from the plurality of pre-formed denture templates is responsive to the at least one of the measurements, wherein the at least one measurement comprises an inter-ridge distance defined as a distance between a center of a right posterior portion of the one edentulous alveolar ridge of the at least one edentulous alveolar ridge of the patient and a center of a left posterior portion of the one edentulous alveolar ridge of the at least one edentulous alveolar ridge of the patient, wherein the pre-formed denture template has an inter-molar distance defined as a distance between a posterior prosthetic tooth of the prosthetic teeth on one side of the base portion and a corresponding posterior prosthetic tooth of the prosthetic teeth on the opposite side of the base portion, and wherein the pre-formed denture template is selected from the plurality of pre-formed denture templates so as to minimize a difference between the inter-ridge distance and the inter-molar distance.

2. The method of producing a denture of claim 1, wherein the method is performed in a single visit.

3. The method of producing a denture of claim 1, wherein the plurality of pre-formed denture templates comprises pre-formed denture templates of at least five different sizes.

4. The method of producing a denture of claim 1, wherein the second material is placed in the u-shaped trough so that it directly contacts the first material.

5. The method of producing a denture of claim 1, wherein the second material solidifies into a rigid layer directly contacting the first material of the base portion.

6. The method of producing a denture of claim 1, wherein the second material solidifies into a semi-rigid layer directly contacting the first material of the base portion.

7. The method of producing a denture of claim 1, wherein seating the pre-formed denture template on the one edentulous alveolar ridge of the at least one edentulous alveolar ridge comprises applying pressure to at least one of an outer surface of the base portion and the prosthetic teeth attached to the base portion.

8. The method of producing a denture of claim 1, wherein the pre-formed denture template comprises at least one of a maxillary pre-formed denture template configured to conform to at least one maxillary structure of the patient comprising at least a palatal vault, and a mandibular pre-formed denture template configured to conform to at least one mandibular structure of the patient comprising at least a lingual space.

9. The method of producing a denture of claim 8, wherein the denture produced comprises a maxillary denture, the method further comprising producing a mandibular denture, wherein the maxillary denture is used to align the mandibular denture within a mouth of the patient during at least one step of producing the mandibular denture.

10. The method of producing a denture of claim 1, wherein the pre-formed denture template is selected from the plurality of pre-formed denture templates so as to minimize a volume between an inner surface of the u-shaped trough and the one edentulous alveolar ridge of the at least one edentulous alveolar ridge.

11. A method of producing a denture, said method comprising:
   selecting for a patient having at least one edentulous alveolar ridge a pre-formed denture template from a plurality of pre-formed denture templates, wherein the plurality of pre-formed denture templates comprises pre-formed denture templates of at least two different sizes, wherein each pre-formed denture template of the plurality of pre-formed denture templates comprises:
     a base portion comprising a u-shaped trough generally in the shape of an alveolar ridge and being configured to at least partially accept one edentulous alveolar ridge of the at least one edentulous alveolar ridge into the u-shaped trough, wherein the base portion is formed out of a first material; and
     prosthetic teeth attached to the base portion;
   wherein the pre-formed denture template is selected from the pre-formed denture templates of at least two different sizes to generally correspond to a size of the one edentulous alveolar ridge of the at least one edentulous alveolar ridge;
   placing a second material inside the u-shaped trough, wherein the second material placed inside the u-shaped trough;

positioning the u-shaped trough containing the second material over the one edentulous alveolar ridge of the at least one edentulous alveolar ridge;

seating the pre-formed denture template on the one edentulous alveolar ridge of the at least one edentulous alveolar ridge such that the one edentulous alveolar ridge of the at least one edentulous alveolar ridge is pressed into the second material contained within the u-shaped trough thereby conforming a portion of the second material contained within the u-shaped trough to the one edentulous alveolar ridge of the at least one edentulous alveolar ridge; and allowing the second material to irreversibly solidify into a rigid negative of the one edentulous alveolar ridge of the at least one edentulous alveolar ridge; measuring at least one dimension of the one edentulous alveolar ridge of the at least one edentulous alveolar ridge to obtain at least one measurement of the at least one dimension, wherein the step of selecting the pre-formed denture template from the plurality of pre-formed denture templates is responsive to the at least one of the measurements, wherein the at least one measurement comprises an inter-ridge distance defined as a distance between a center of a right posterior portion of the one edentulous alveolar ridge of the at least one edentulous alveolar ridge of the patient and a center of a left posterior portion of the one edentulous alveolar ridge of the at least one edentulous alveolar ridge of the patient, wherein the pre-formed denture template has an inter-molar distance defined as a distance between a posterior prosthetic tooth of the prosthetic teeth on one side of the base portion and a corresponding posterior prosthetic tooth of the prosthetic teeth on the opposite side of the base portion, and wherein the pre-formed denture template is selected from the plurality of pre-formed denture templates so as to minimize a difference between the inter-ridge distance and the inter-molar distance.

12. The method of producing a denture of claim 11, wherein the method is performed in a single visit.

13. The method of producing a denture of claim 11, wherein the plurality of pre-formed denture templates comprises pre-formed denture templates of at least five different sizes.

14. The method of producing a denture of claim 11, wherein the second material is placed in the u-shaped trough so that it directly contacts the first material.

15. The method of producing a denture of claim 11, wherein the second material solidifies into a rigid layer directly contacting the first material of the base portion.

16. The method of producing a denture of claim 11, wherein seating the pre-formed denture template on the one edentulous alveolar ridge of the at least one edentulous alveolar ridge comprises applying pressure to at least one of an outer surface of the base portion and the prosthetic teeth attached to the base portion.

17. The method of producing a denture of claim 11, wherein the pre-formed denture template comprises at least one of a maxillary pre-formed denture template configured to conform to at least one maxillary structure of the patient comprising at least a palatal vault, and a mandibular pre-formed denture template configured to conform to at least one mandibular structure of the patient comprising at least a lingual space.

18. The method of producing a denture of claim 17, wherein the denture produced comprises a maxillary denture, the method further comprising producing a mandibular denture, wherein the maxillary denture is used to align the mandibular denture within a mouth of the patient during at least one step of producing the mandibular denture.

19. The method of producing a denture of claim 11, wherein the pre-formed denture template is selected from the plurality of pre-formed denture templates so as to minimize a volume between an inner surface of the u-shaped trough and the one edentulous alveolar ridge of the at least one edentulous alveolar ridge.

* * * * *